United States Patent [19]

Skotnicki et al.

[11] Patent Number: 4,719,302

[45] Date of Patent: Jan. 12, 1988

[54] 1,7-PHENANTHROLINES AND THEIR USE AS ANTIFUNGAL AGENTS

[75] Inventors: Jerauld S. Skotnicki, Chadds Ford; Donald P. Strike, St. Davids; Bruce A. Steinbaugh, King of Prussia, all of Pa.

[73] Assignee: American Home Products Corporation, New York, N.Y.

[21] Appl. No.: 25,316

[22] Filed: Mar. 13, 1987

[51] Int. Cl.$^4$ .......................... C07D 471/04
[52] U.S. Cl. ........................................ 546/88
[58] Field of Search .......................... 546/88

[56] References Cited

PUBLICATIONS

Shaw Waring, Chem. Abstracts, vol. 78; 29744s (1973).
Hirao et al., Chem. Abstracts, vol. 102; 95565z (1985).
*Memoirs Kyushu Inst. Technol. Eng.*, 14, 23–27 (1984).

Primary Examiner—Henry R. Jiles
Assistant Examiner—J. Richter
Attorney, Agent, or Firm—George Tarnowski

[57] ABSTRACT

There are disclosed compounds having the formula

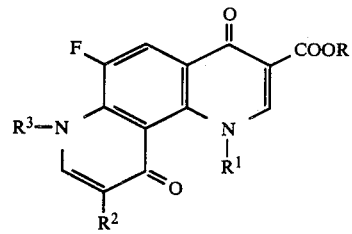

wherein
R is hydrogen or lower alkyl;
$R^1$ is hydrogen, lower alkyl, lower alkenyl, lower alkynyl, phenyl or any of the foregoing substituted with halo;
$R^2$ is hydrogen, carboxy or lower alkoxy carbonyl; and
$R^3$ is hydrogen, lower alkyl, lower alkenyl, lower alkynyl or any of the foregoing substituted with carboxy, methoxycarbonyl, hydroxy, amino, di-lower alkyl amino, cyano, nitro or lower alkoxy;

and their use as antifungal agents.

7 Claims, No Drawings

1,7-PHENANTHROLINES AND THEIR USE AS ANTIFUNGAL AGENTS

The invention relates to tricyclic fluoroquinolone derivatives and their use as antifungal agents.

The invention is directed to compounds having the formula

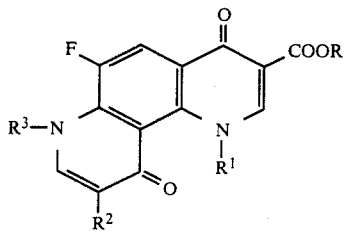

wherein
R is hydrogen or lower alkyl;
$R^1$ is hydrogen, lower alkyl, lower alkenyl, lower alkynyl, phenyl or any of the foregoing substituted with halo;
$R^2$ is hydrogen, carboxy or lower alkoxy carbonyl; and
$R^3$ is hydrogen, lower alkyl, lower alkenyl, lower alkynyl or any of the foregoing substituted with carboxy, methoxycarbonyl, hydroxy, amino, di-lower alkyl amino, cyano, nitro or lower alkoxy.

The term "halo" refers to fluoro, chloro and bromo. The terms "lower alkyl," "lower alkenyl," "lower alkynyl" and "lower alkoxy" refer to straight or branched chain moieties having 1-6 carbon atoms.

The preferred compounds are those wherein R is hydrogen or ethyl, $R^1$ is hydrogen or ethyl, $R^2$ is hydrogen, carboxy or ethoxycarbonyl and $R^3$ is hydrogen or ethyl.

The compounds of the invention can be prepared in the following manner:

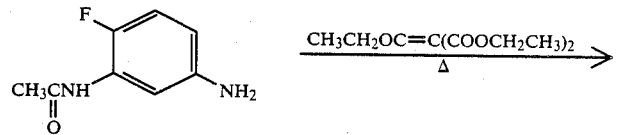

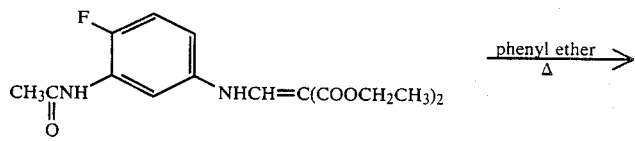

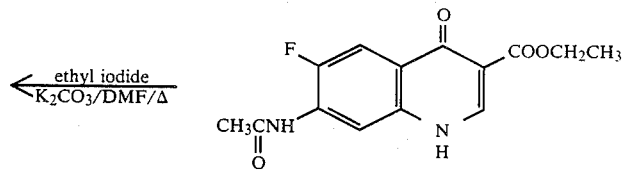

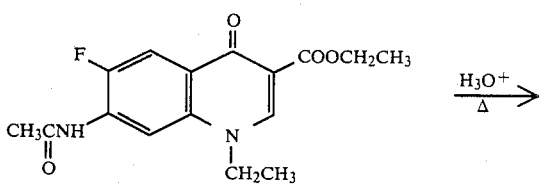

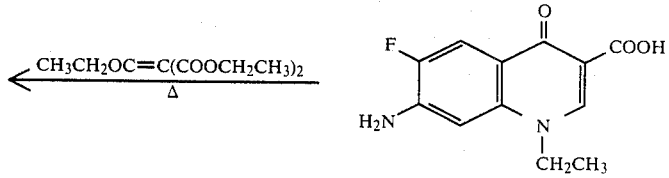

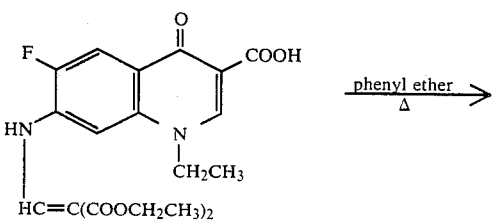

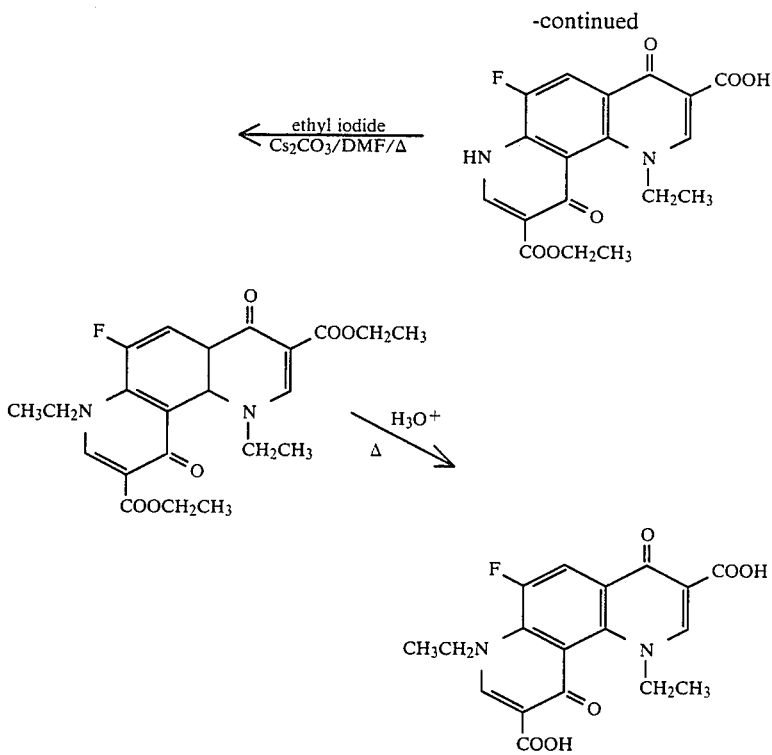

In an alternative reaction scheme, the molecule can be constructed by first forming the lower left and pyridone ring. In this instance, the starting material is structured as follows:

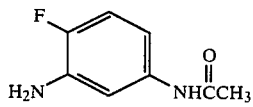

In all other respects the reaction scheme is identical to the one outlined above.

The starting 4-(N-acetylamino)-2-amino-1-fluorobenzene and 2-(N-acetylamino)-4-amino-1-fluorobenzene are commercially available or can be prepared by conventional methods known in the chemical literature. The other reactants and solvents used in the preparative scheme are all commercially available.

The compounds of the invention are useful agents in combatting fungi. For example, the compounds have been found active against a variety of pathogenic fungi, such as *Candida albicans, Cryptococcus neoformans, Trichophyton mentagrophytes, Histoplasma capsulatum* and *Blastomyces dermatitidis*. Because of their antifungal activity, the compounds of the invention are useful in the destruction and prevention of the growth of fungi and as such can be effectively used in the treatment of subjects suffering from fungal infection.

Because of their antifungal properties, the compounds of the invention can be formulated into therapeutically valuable compositions comprising compounds of the invention and pharmacologically acceptable carriers. The latter term contemplates usual and customary substances employed to formulate solid, oral unit dosages for pharmacological purposes. The term also includes those substances employed to formulate either in unit dose or multidose form, oral and injectable suspensions and solutions, either directly or for reconstitution before administration.

To formulate dosages for administration according to this invention the compounds of the invention can be compounded into oral dosage forms such as tablets, capsules and the like. This is done by combining the compounds with conventional carriers, such as magnesium carbonate, magnesium stearate, talc, sugar, lactose, pectin, dextrin, starch, gelatin, tragacanth, methylcellulose, sodium carboxymethylcellulose, cellulose, low melting wax, cocoa butter, and the like. Diluents, flavoring agents, solubilizers, lubricants, suspending agents, binders, tablet-disintegrating agents and the like may be employed. The active ingredient may be encapsulated with or without other carriers. In all cases, the proportion of active ingredients in said compositions both solid and liquid will be at least sufficient to impart antifungal activity thereto on oral administration.

The compounds may also be injected parenterally, in which case they are used in the form of a sterile solution containing other solutes, for example, enough saline or glucose to make the solution isotonic. The compounds may also be used topically and for this purpose they may be formulated in the form of dusting powders, solutions, creams or lotions in pharmaceutically acceptable vehicles, which are applied to affected portions of the skin.

The dosage requirements vary with the particular compositions employed, the route of administration, the severity of the symptoms presented and the particular subject being treated. Treatment will generally be limited with small dosages less than the optimum dose of the compound. Thereafter, the dosage is increased until the optimum effect under the circumstances is reached. In general, the compounds of the invention are most desirably administered at a concentration level that will generally afford effective results without causing any harmful or deleterious side effects.

The antifungal activity of the compounds of the invention may be demonstrated by a standard pharmacological procedure which is described fully following the below presented examples directed to the preparation of the compounds useful in the invention.

EXAMPLE 1

1-Ethyl-6-fluoro-1,4,7,10-tetrahydro-4,10-dioxo-1,7-phenanthroline-3,9-dicarboxylic acid 9-ethyl ester (A)

[[[3-(Acetylamino)-4-fluorophenyl]amino]methylene]-propanedioic acid diethyl ester A mixture of 26.56 g (0.1579 mol) of 2-(N-acetylamino)-4-amino-1-fluorobenzene, 35.89 ml (0.1776 mol) of diethyl ethoxymethylenemalonate, and 30 ml of toluene is stirred at 130° C. for 3 hours. After cooling, the precipitate which forms is triturated with ether to yield 50.64 g (94.8%) of title compound as a white solid:

IR (KBr) 3325, 1678, 1640, 1610 and 1575 cm$^{-1}$;
NMR (CDCl$_3$) δ 10.95 (br, 1H), 8.43 (d, 1H), 8.23 (m, 1H), 7.77 (br, 1H), 7.35–6.65 (m, 2H), 4.30 (m, 4H), 2.27 (s, 3H), 1.35 (m, 6H).

(B)

7-(Acetylamino)-6-fluoro-1,4-dihydro-4-oxo-3-quinolinecarboxylic acid ethyl ester A mixture of 50.37 g (0.1489 mol) of (A) above and 500 ml of phenyl ether is stirred at 260° C. for 9 hours. After cooling, the precipitate is collected and triturated with ether to yield 28.69 g (65.9%) of title compound as a tan solid:

IR (KBr) 3420 (br), 3100, 1685, 1612, and 1520 cm$^{-1}$;
NMR (DMSO-d$_6$) δ 8.45 (m, 1H), 7.95–7.20 (m, 2H), 4.17 (q, 2H), 2.14 (m, 3H), 1.22 (t, 3H).

(C)

7-(Acetylamino)-1-ethyl-6-fluoro-1,4-dihydro-4-oxo-3-quinolinecarboxylic acid ethyl ester A mixture of 28.43 g (0.0973 mol) of (B) above 33.81 g (0.245 mol) of K$_2$CO$_3$, 39.13 ml (0.489 mol) of ethyl iodide, and 175 ml of dimethylformamide is stirred overnight at 80°–90° C. After cooling, the mixture is diluted with water and extracted with methylene chloride. The combined extracts are washed with water and brine, dried over Na$_2$SO$_4$, and concentrated under reduced pressure. The residue is triturated with ether to furnish 12.88 g (41.3%) of title compound as a tan solid: m.p. 177°–180° C.;

IR (KBr) 3420 (br), 1675 and 1615 cm$^{-1}$;
NMR (CDCl$_3$) δ 9.17 (br, 1H), 8.74 (d, 1H), 8.48 (s, 1H), 8.02 (d, 1H), 4.29 (m, 4H), 2.38 (s, 3H), 1.45 (m, 6H); MS m/e 321 (M+1).

(D)

7-Amino-1-ethyl-6-fluoro-1,4-dihydro-4-oxo-3-quinolinecarboxylic acid

A mixture of 12.05 g (0.0376 mol) of (C) above and 150 ml of 6N HCl is stirred overnight at 90°–100° C. After cooling, the mixture is concentrated under reduced pressure. The residue is triturated with cold ethanol to yield 6.766 g (71.9%) of title compound as a tan solid:

IR (KBr) 3440, 3340, 1705, and 1625 cm$^{-1}$;
NMR (DMSO-d$_6$) δ 9.00–8.00 (m, 4H), 7.70 (d, 1H), 7.08 (d, 1H), 4.33 (q, 2H), 1.38 (t, 3H); MS m/e 251 (M+1).

(E)

[[(3-Carboxy-1-ethyl-6-fluoro-1,4-dihydro-4-oxo-7-quinolinyl)amino]methylene]propanedioic acid diethyl ester A mixture of 4 g (0.016 mol) of (D) above, 3.23 ml (0.016 mol) of diethyl ethoxymethylenemalonate, and 35 ml of toluene is stirred at 120°–130° C. overnight. After cooling, the mixture is triturated with ether to yield 4.997 g (74.4%) of title compound as a yellow solid:

IR (KBr) 1690, 1610 and 1440;
NMR (DMSO-d$_6$) δ 11.12 (d, 1H), 9.04 (s, 1H), 8.74 (d, 1H), 8.12 (m, 2H), 4.69 (q, 2H), 4.25 (m, 4H), 1.46 (t, 3H), 1.28 (t, 6H); MS m/e 421 (M+1).

(F)

1-Ethyl-6-fluoro-1,4,7,10-tetrahydro-4,10-dioxo-1,7-phenanthroline-3,9-dicarboxylic acid 9-ethyl ester A mixture of 4.81 g (0.0114 mol) of (E) above and 50 ml of phenyl ether is stirred at 260° C. for 1 hour. After cooling, the precipitate is collected and partitioned between methylene chloride and a sodium bicarbonate solution. The solid which forms in the bicarbonate layer is washed with water and ether to give 0.961 g (23.3%) of title compound as a tan solid:

IR (KBr) 3440 (br), 1710 (br), and 1600 cm$^{-1}$;
NMR (DMSO-d$_6$) δ 13.06 (br-s, 1H), 9.04 (s, 1H), 8.41 (s, 1H), 8.19 (m, 1H), 4.49 (m, 2H), 4.28 (m, 2H), 1.31 (t, 3H), 1.12 (t, 3H); MS m/e 375 (M+1).

EXAMPLE 2

1,7-Diethyl-6-fluoro-1,4,7,10-tetrahydro-4,10-dioxo-1,7-phenanthroline-3,9-dicarboxylic acid diethyl ester A mixture of 0.813 g (2.17 mmol) of the compound of Example 1(F) above, 0.869 ml (10.9 mmol) of ethyl iodide, 3.528 g (10.9 mmol) of Cs$_2$CO$_3$, and 15 ml of dimethylformamide is stirred overnight at 80° C. After cooling, the mixture is diluted with water and extracted with methylene chloride. The combined extracts are washed with water and brine, dried over Na$_2$SO$_4$, and concentrated under reduced pressure to yield 1.16 g (100%) of title compound as brown oil-glass:

IR (neat) 1722, 1675, and 1610 cm$^{-1}$;
NMR (DMSO-d$_6$) δ 8.74 (s, 1H), 8.68 (s, 1H), 8.14 (d, 1H), 4.6–4.16 (m, 8H), 1.45 (t, 3H), 1.31 (m, 6H), 1.09 (t, 3H); MS m/e 431 (M+1).

EXAMPLE 3

1,7-Diethyl-6-fluoro-1,4,7,10-tetrahydro-4,10-dioxo-1,7-phenanthroline-3,9-dicarboxylic acid A mixture of 0.935 g (2.17 mmol) of the compound of Example 2 and 20 ml of 6N HCl is stirred at 90° C. for 4 hours. After cooling, the mixture is concentrated under reduced pressure. The residue is triturated with cold ethanol to furnish 0.334 g (41.1%) of title compound as a tan solid:

IR (KBr) 1722, 1608, and 1440 cm$^{-1}$;
NMR (DMSO-d$_6$) δ 9.12 (s, 1H), 9.10 (s, 1H), 8.37 (d, 1H), 4.71 (m, 2H), 4.42 (m, 2H), 1.51 (t, 3H), 1.12 (t, 3H); MS m/e 375 (M+1).

EXAMPLE 4

7-Ethyl-6-fluoro-1,4,7,10-tetrahydro-4,10-dioxo-1,7-phenanthroline-3-carboxylic acid ethyl ester

(A)

[[[5-(Acetylamino)-2-fluorophenyl]amino]methylene]-propanedioic acid diethyl ester A mixture of 1.9 g (0.0113 mol) of 4-(N-acetylamino)-2-amino-1-fluorobenzene, 2.6 ml (2.78 g/0.0129 mol) of diethyl ethoxymethylenemalonate, and 4 ml of toluene is stirred at reflux for three hours, then allowed to cool to ambient temperature. The resulting precipitate is triturated with ether to give 3.29 g (84%) of title compound:

IR (KBr) 3250, 1685, 1650, 1610, and 1580 cm$^{-1}$;

NMR (DMSO-d$_6$) δ 10.8 (br-d, 1H, exchangeable), 10.1 (br-s, 1H, exchangeable), 8.35 (br-d, 1H), 7.9–7.7 (m, 1H), 7.4–7.2 (m, 1H), 4.4–4.0 (m, 4H), 2.07 (s, 3H9, 1.30 (t, 3H), and 1.27 (t, 3H); MS m/e 339 (M+1).

(B)

5-(Acetylamino)-8-fluoro-1,4-dihydro-4-oxo-3-quinolinecarboxylic acid ethyl ester A solution of 3.0 g (0.0089 mol) of (A) above and 35 ml of phenyl ether is stirred at 250°–260° C. for one hour, then allowed to cool to ambient temperature. The resulting precipitate is triturated with ether to give 1.8 g (69%) of title compound:

IR (KBr) 3200 (br), 1690, 1660, and 1620 cm$^{-1}$;

NMR (DMSO-d$_6$) δ 13.2 (br-s, 1H, exchangeable), 8.6–8.3 (m, 2H, exchangeable), 7.7–7.4 (m, 2H), 4.25 (q, 2H), 2.17 (s, 3H), and 1.30 (t, 3H); MS m/e 293 (M+1).

(C)

5-(Acetylamino)-1-ethyl-8-fluoro-1,4-dihydro-4-oxo-3-quinolinecarboxylic acid ethyl ester A mixture of 4.6 g (0.0157 mol) of (B) above, 6.5 g (0.0470 mol) of K$_2$CO$_3$, 4 ml (7.8 g/0.050 mol) of ethyl iodide, and 40 ml of dimethylformamide is stirred at 80°–90° C. overnight. The reaction mixture is allowed to cool to ambient temperature, diluted with water and extracted with methylene chloride. The combined extracts are washed with brine, dried over Na$_2$SO$_4$, and concentrated in vacuo. Trituration of the residue with ether furnishes 1.35 g (27%) of title compound:

IR (KBr) 1670 and 1610 cm$^{-1}$;

NMR (DMSO-d$_6$) δ 13.6 (br-s, 1H, exchangeable), 8.6–8.4 (m, 2H), 7.8–7.45 (m, 1H), 4.5–4.1 (m, 4H), 2.15 (s, 3H), and 1.45–1.20 (m, 6H); MS m/e 321 (M+1).

(D)

5-Amino-1-ethyl-8-fluoro-1,4-dihydro-4-oxo-3-quinolinecarboxylic acid

A mixture of 1.2 g (0.037 mol) of (C) above and 20 ml of 6N HCl solution is stirred at 100° C. overnight. The reaction mixture is allowed to cool to ambient temperature and is concentrated in vacuo. The residue is triturated with cold ethanol to give 785 mg (85%) of title compound:

IR (KBr) 3400, 3700–2500, 1710, and 1605 cm$^{-1}$;

NMR (DMSO-d$_6$/D$_2$O) δ 8.55 (s, 1H), 7.5–7.15 (m, 1H), 6.7–6.45 (m, 1H), 4.5–4.2 (m, 2H), and 1.3 (t, 3H); MS m/e 251 (M+1).

(E)

[[(3-Carboxy-1-ethyl-8-fluoro-1,4-dihydro-4-oxo-5-quinolinyl)amino]methylene]propanedioic acid diethyl ester A mixture of 500 mg (0.002 mol) of (D) above, 0.5 ml (5.35 mg/0.025 mol) of diethyl ethoxymethylenemalonate, and 4 ml of toluene is stirred at 120° C. for 8 hours, then allowed to cool to ambient temperature. Trituration of the residue with ether affords 720 mg (86%) of title compound:

IR (KBr) 3140, 2700–2500, 1730, 1695, 1660, and 1620 cm$^{-1}$;

NMR (DMSO-d$_6$/D$_2$O) δ 8.88 (s, 1H), 8.46 (s, 1H), 7.9–7.76 (m, 1H), 7.64–7.54 (m, 1H), 4.66–4.54 (m, 2H), 4.3 (q, 2H), 4.2 (q, 2H), 1.48 (t, 3H), 1.30 (t, 3H), and 1.28 (t, 3H); MS m/e 421 (M+1).

Analysis for: C$_{20}$H$_{21}$N$_2$O$_7$F: Calculated: C, 57.14; H, 5.03; N, 6.67. Found: C, 57.48; H, 4.94; N, 6.42.

(F)

7-Ethyl-6-fluoro-1,4,7,10-tetrahydro-4,10-dioxo-1,7-phenanthroline-3-carboxylic acid ethyl ester A solution of 600 mg (0.0014 mol) of (E) above and 6 ml of Ph$_2$O is stirred at 250°–260° C. for one hour, then allowed to gradually cool to ambient temperature. The precipitate is collected, dissolved in methylene chloride and treated with saturated sodium bicarbonate solution. The organic phase is dried (Na$_2$SO$_4$), and concentrated in vacuo. The residue is triturated with ether to give 78 mg (17%) of title compound:

IR (KBr) 1715, 1670, and 1620 cm$^{-1}$;

NMR (DMSO-d$_6$) δ 14.75 (br-s), 8.84 (d, 1H), 8.30 (d, 1H), 8.18 (d, 1H), 6.54 (d, 1H), 4.58–4.44 (m, 2H), 4.26 (q, 2H), 1.44 (t, 3H), and 1.30 (t, 3H); MS m/e 331 (M+1).

EXAMPLE 5

7-Ethyl-6-fluoro-1,4,7,10-tetrahydro-4,10-dioxo-1,7-phenanthroline-3,9-dicarboxylic acid 3-ethyl ester The aqueous phase obtained in Example 4 is acidifed using 1N HCl solution and extracted with methylene chloride. The extracts are dried (Na$_2$SO$_4$), and concentrated in vacuo. The residue is triturated with ether to furnish 120 mg (23%) of title compound:

IR (KBr) 3180, 1710, 1665, and 1620 cm$^{-1}$;

NMR (DMSO-d$_6$) δ 14.2 (br-s, 1H, exchangeable), 13.7 (d, 1H, exchangeable), 9.18 (s, 1H), 8.78 (d, 1H), 8.30 (d, 1H), 4.82–4.64 (m, 2H), 4.28 (q, 2H), 1.5 (t, 3H), and 1.3 (t, 3H); MS m/e 375 (M+1).

EXAMPLE 6

7-Ethyl-6-fluoro-1,4,7,10-tetrahydro-4,10-dioxo-1,7-phenanthroline-3,9-dicarboxylic acid diethyl ester A mixture of 940 mg (0.025 mol) of the compound of Example 5, 2.5 g (0.0181 mol) of K$_2$CO$_3$, 2.5 ml (4.9 g/0.031 mol) of ethyl iodide, and 10 ml of dimethylformamide is stirred at 65° C. overnight. The reaction mixture is allowed to cool to ambient temperature, diluted with water, and extracted with ethyl acetate. The combined organic extracts are washed with brine, dried over Na$_2$SO$_4$, and concentrated in vacuo to provide an oily solid. Trituration with cold ethanol yields 150 mg (15%) of title compound:

IR (KBr) 3440 (br), 1735, 1690, 1640, and 1620 cm$^{-1}$;

NMR (DMSO-d₆) δ 14.47 (d, 1H, exchangeable), 8.82 (s, 1H), 8.79 (d, 1H), 8.22 (d, 1H), 4.66–4.52 (m, 2H), 4.34 (q, 2H), 4.26 (q, 2H), 1.46 (t, 3H), 1.32 (t, 3H), and 1.26 (t, 3H); MS m/e 403 (M+1).

EXAMPLE 7

The compounds of the invention are tested to determine their antifungal activity. The assay procedure is as follows:

The compounds to be tested are solubilized or suspended in appropriate reagent and further diluted in sterile distilled water to provide a range of concentrations from 200 to 10 μg/ml. 20 Lambda portions are placed on sterile dried ¼ inch paper discs and allowed to dry for 20–30 minutes. Agar plates with a 10 ml base layer are seeded with the fungi in a 4 ml seed layer and allowed to solidify. The impregnated discs are then placed on the seeded agar surface and incubated for the time required for the particular culture.

The representative fungi are:

| | |
|---|---|
| Candida albicans | ATCC 10231 |
| Cryptococcus neoformans | ATCC 14115 |
| Histoplasma capsulatum | ATCC 11407-yeast phase |
| Blastomyces dermatitidis | ATCC 28839-yeast phase |
| Trichophyton mentagrophytes | ATCC 9533 |

All are human pathogens; the first four cause serious systemic mycotic infections as well as local. The trychophyton culture is mainly a dermatophyte.

The zones of inhibition are measured and the results for the given concentration of compound are tabulated in Table 1 below.

TABLE 1

| | Minimum Inhibitory Concentration (μg/ml) | | | | |
|---|---|---|---|---|---|
| Example (Compound) | Candida Albicans ATCC 10231 | Cryptococcus Neoformans ATCC 14115 | Trichophyton Mentagrophytes ATCC 9533 | Histoplasma Capsulatum Yeast Phase ATCC 11407 | Blastomyces Dermatitidis Yeast Phase ATCC 28839 |
| 1 | 32 | 64 | 64 | 32 | 32 |
| 2 | >64 | >64 | >64 | 64 | 64 |
| 3 | >64 | >64 | >64 | 64 | 64 |
| 4 | >256 | >256 | >256 | >256 | >256 |
| 5 | >256 | >256 | >256 | >256 | >256 |
| 6 | >64 | >64 | >64 | 64 | 64 |

The results show that the compounds of the invention have antifungal activity against a variety of pathogenic fungi.

What is claimed is:

1. A compound having the formula

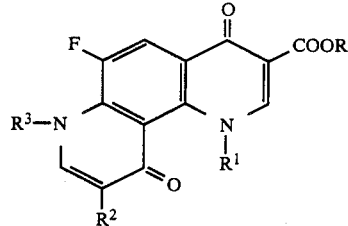

wherein
R is hydrogen or lower alkyl;
R¹ is hydrogen or lower alkyl, lower alkenyl, lower alkynyl, phenyl or any of the foregoing substituted with halo;
R² is hydrogen, carboxy or lower alkoxy carbonyl; and
R³ is hydrogen, lower alkyl, lower alkenyl, lower alkynyl or any of the foregoing substituted with carboxy, methoxycarbonyl, hydroxy, amino, di-lower alkyl amino, cyano, nitro or lower alkoxy.

2. The compound of claim 1, having the name 1-ethyl-6-fluoro-1,4,7,10-tetrahydro-4,10-dioxo-1,7-phenanthroline-3,9-dicarboxylic acid 9-ethyl ester.

3. The compound of claim 1, having the name 1,7-diethyl-6-fluoro-1,4,7,10-tetrahydro-4,10-dioxo-1,7-phenanthroline-3,9-dicarboxylic acid diethyl ester.

4. The compound of claim 1, having the name 1,7-diethyl-6-fluoro-1,4,7,10-tetrahydro-4,10-dioxo-1,7-phenanthroline-3,9-dicarboxylic acid.

5. The compound of claim 1, having the name 7-ethyl-6-fluoro-1,4,7,10-tetrahydro-4,10-dioxo-1,7-phenanthroline-3-carboxylic acid ethyl ester.

6. The compound of claim 1, having the name 7-ethyl-6-fluoro-1,4,7,10-tetrahydro-4,10-dioxo-1,7-phenanthroline-3,9-dicarboxylic acid 3-ethyl ester.

7. The compound of claim 1, having the name 7-ethyl-6-fluoro-1,4,7,10-tetrahydro-4,10-dioxo-1,7-phenanthroline-3,9-dicarboxylic acid diethyl ester.

* * * * *